(12) United States Patent
Baker et al.

(10) Patent No.: US 8,388,562 B2
(45) Date of Patent: Mar. 5, 2013

(54) FOOTWEAR

(75) Inventors: Dominic John Baker, Bucks (GB); Leslie Lindsay, Westbury (GB)

(73) Assignee: Diabetic Boot Company Limited, Brackley, Northamptonshire (GB)

( * ) Notice: Subject to any disclaimer, the term of this patent is extended or adjusted under 35 U.S.C. 154(b) by 304 days.

(21) Appl. No.: 12/738,929

(22) PCT Filed: Oct. 23, 2008

(86) PCT No.: PCT/GB2008/003600
§ 371 (c)(1),
(2), (4) Date: Apr. 20, 2010

(87) PCT Pub. No.: WO2009/053704
PCT Pub. Date: Apr. 30, 2009

(65) Prior Publication Data
US 2010/0210983 A1 Aug. 19, 2010

(30) Foreign Application Priority Data

Oct. 23, 2007 (GB) .................................. 0720706.1

(51) Int. Cl.
*A61H 7/00* (2006.01)
(52) U.S. Cl. ........................................................ 601/148
(58) Field of Classification Search .................... 60/477; 601/32, 148–153, 27; 602/13
See application file for complete search history.

(56) References Cited

U.S. PATENT DOCUMENTS

| | | | |
|---|---|---|---|
| 4,197,706 A | * | 4/1980 | Blake .............................. 60/477 |
| 4,502,470 A | | 3/1985 | Kiser et al. |
| 4,577,626 A | | 3/1986 | Marukawa et al. |

(Continued)

FOREIGN PATENT DOCUMENTS

| DE | 3417497 A1 | 11/1985 |
|---|---|---|
| EP | 1 593 360 A2 | 11/2005 |
| WO | 97/36508 A1 | 10/1997 |
| WO | 2006/061397 A2 | 6/2006 |

OTHER PUBLICATIONS 2 pages from emedicinehealth.com downlaoded Apr. 3, 2012.*

(Continued)

*Primary Examiner* — Jackie Ho
*Assistant Examiner* — Mark Wardas
(74) *Attorney, Agent, or Firm* — Dardi & Herbert, PLLC; Curtis B. Herbert

(57) ABSTRACT

The present invention relates to footwear and in particular, but not necessarily restricted thereto, relates to footwear for those with diabetes and, in particular, with ulcers of the sole. The present invention seeks to address some of the problems encountered by prior art limb compression devices and methods. In particular the present invention seeks to provide a boot which can stimulate blood flow. A further object to the invention is to provide a boot with a sole which is adaptable to conform with various shapes and conditions of human feet. The present invention also seeks to provide a new type of footwear that has a therapeutic benefit for diabetic patients with circulatory problems in their foot, and also enables the technique of "off loading" the foot to assist in the healing of any wounds present. The present invention relates to a method for aiding arterial and venous flow from the limb of an ambulatory patient comprising the step of applying pressure to one or more areas of the soft tissue of an underside portion of the foot.

10 Claims, 5 Drawing Sheets

U.S. PATENT DOCUMENTS

| | | | |
|---|---|---|---|
| 4,624,244 A | 11/1986 | Taheri | |
| 4,941,458 A | 7/1990 | Taheri | |
| 5,218,954 A | 6/1993 | van Bemmelen | |
| 6,589,194 B1* | 7/2003 | Calderon et al. | 601/151 |
| 2003/0013997 A1 | 1/2003 | Raju | |
| 2004/0171971 A1* | 9/2004 | Ravikumar et al. | 601/32 |

OTHER PUBLICATIONS

Armstrong et al., "Improvement in Healing with Aggressive Edema Reduction After Debridement of Foot Infection in Persons with Diabetes", Arch Surg. 135:1405-1409 (Dec. 2000).

* cited by examiner

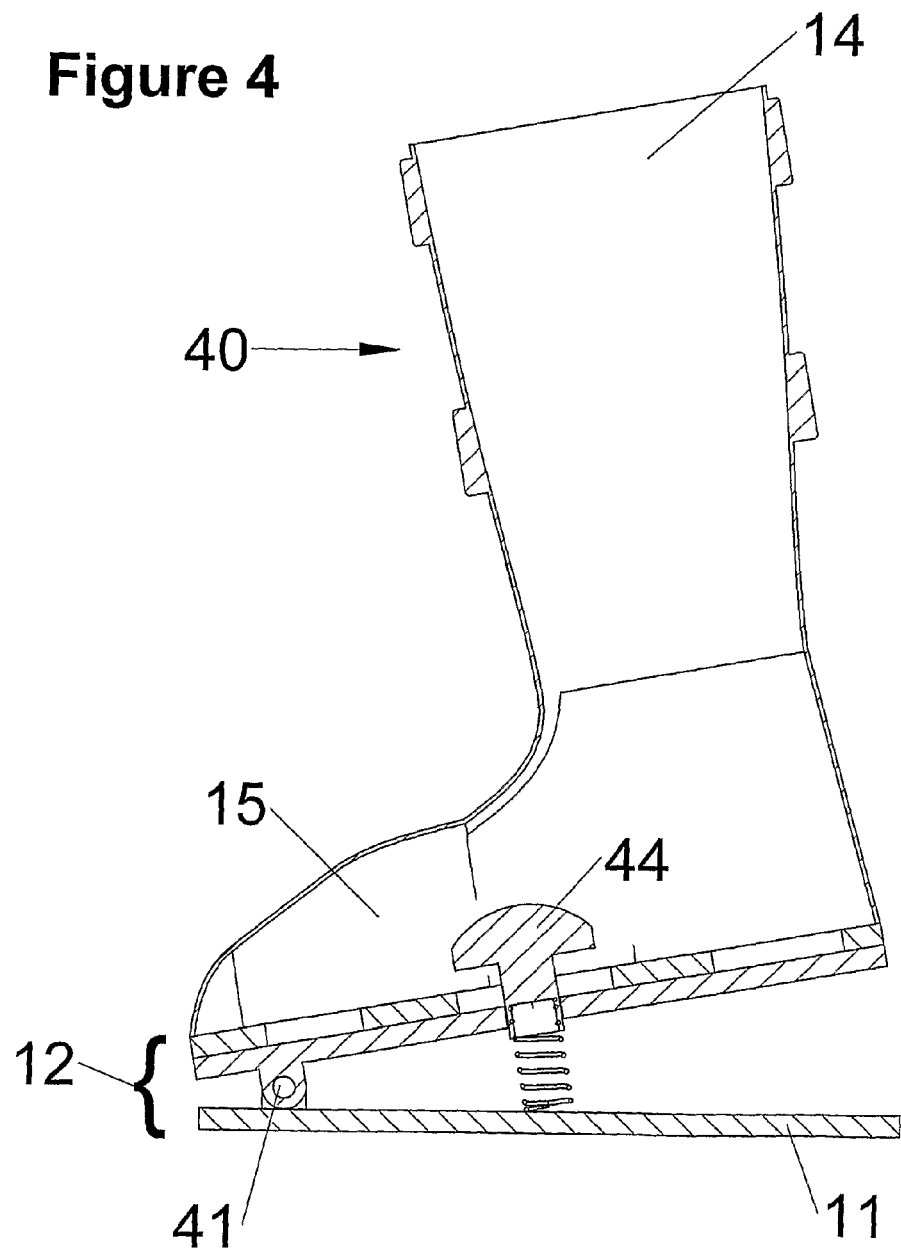

FOOTWEAR

RELATED APPLICATIONS

This application is a national stage filing of PCT Application No. PCT/GB2008/003600 filed Oct. 23, 2008, which claims priority to United Kingdom GB0720706.1 filed Oct. 23, 2007.

FIELD OF THE INVENTION

The present invention relates to footwear and in particular, but not necessarily restricted thereto, relates to footwear for those with diabetes and, in particular, with ulcers of the sole. The present invention also relates to a method for aiding cardiocepital venous flow from the foot and leg of an ambulatory patient who is suffering from diseased foot and leg veins which results in venous hypertension.

BACKGROUND AND INTRODUCTION TO THE INVENTION

Improvement of arterial blood flow, in patients with obstruction of the arteries to the leg, is usually obtained by surgically bypassing the occluded arteries, or by removing obstructions with devices that are inserted into the blood vessel. In elderly patients who have undergone multiple vascular procedures, the deterioration of arterial blood flow can lead to severe pain (ischemic neuritis), tissue loss (arterial ulcers) or toe loss (gangrene). When the arteries cannot be repaired anymore, this situation may lead to leg amputation.

Blood flow in patient's extremities, particularly the legs, markedly decreases during extended terms of confinement. Such pooling or stasis is particularly acute in surgery and during recovery periods immediately thereafter.

In the past, numerous devices and methods have been disclosed for aiding cardiocepital venous flow to prevent venous hypertension. These devices and methods usually included the use of boots placed around the foot and leg and pressure was applied to the foot and leg. However, the prior devices were extremely cumbersome and usually required the patient to remain immobile. In addition, the prior devices did not concentrate the pressure in those areas in which it was most effective, namely, the soft tissue areas of the foot and leg, and therefore they did not operate efficiently. Also, the prior devices and method could not be used for an ambulatory patient because of the need to be connected with stationary equipment, which in turn needs to be connected to a mains power supply.

Certain treatments comprise of a massager composed of a linear compressor having a piston reciprocated by force of electromagnetic attraction to produce compressed air at a safe pressure with a relatively small difference between the rated pressure and the maximum pressure, a distributor for allowing the compressed air fed from the compressor to be selectively discharged therefrom and a bag having a plurality of air tight sections which are successively expanded by receiving the compressed air fed from the distributor. For example, U.S. Pat. No. 4,577,626 relates to a massager which utilizes compressed air at a safe pressure and has a simple structure and easy operation.

Other devices have comprised pressure-fluid massage machines and devices which have been provided with a bag means of rubber or the like, which is wound around a portion to be treated on the subject and expanded by supplying thereto a pressure fluid such as compressed air to exert massaging pressure upon the portion to be treated, thereby massaging the subject. In the massager of this type, to improve the massaging effect, the bag means is partitioned off into air-tight sections so that a pressure fluid can successively be fed into the air-tight sections by use of a distributing valve to give the massaging pressure to successive parts of the portion to be treated on the subject in consequence of the expansion of the bag means.

U.S. Pat. No. 5,218,954 teaches of a device which operates by providing simultaneous and rapid compression of the soft tissues of the calf, ankle and foot, thereby completely and instantly emptying the veins, and reducing venous pressure to zero in a sitting patient position. Upon rapid deflation of the boot, the reduced venous pressure results in an increased driving pressure for the arterial blood flow. The increased arterial blood flow will occur approximately one second after deflation, and will last for approximately 4-14 seconds. The compression phase itself does not improve arterial flow, but impedes arterial flow; therefore compression is kept as short as possible. The design of the compression boot is fashioned for this purpose. A stiff, non-elastic outer case for the lower leg and foot reduces the amount of fluid (air) needed to inflate the relatively small bladder.

One use for the above mentioned devices is the prevention of deep venous thrombosis (DVT) which sometimes occurs in surgical patients when they are confined to bed. When a DVT occurs, the valves that are located within the veins of the leg can be damaged which in turn can cause stasis and high pressure in the veins of the lower leg.

Patients who have this condition often have leg swelling (oedema) and tissue breakdown (venous stasis ulcer) in the lower leg.

Certain manufacturers provide cuff-like arrangements and similar types of devices;—whilst being designed for and providing assistance to patients with DVT, have been found to provide benefit in diabetic patients. However, a problem exists in that the equipment is electrically powered, and a patient is required to remain immobile for at least 6 hours per day during therapy.

U.S. Pat. No. 4,502,470 provides a physiologic device having a fluid filled compartment. This is surrounded by an outer sheath fastened to the foot. The sheath holds the compartment under the instep and directs the hydraulic forces into the ankle and lower leg. Pressure produced by walking on the fluid compartment is used to compress the lower leg. This prevents swelling and it can heal ulcers due to bad veins. U.S. Pat. No. 5,218,954 teaches of a device and method for the purpose of increasing arterial blood flow to the lower leg, calf, ankle and foot. The device is a compression boot, or cast, and consists of a mono-compartment bladder enclosed in a non-elastic outer envelope connected to an air compressor with regulator valve, providing fast inflation to pressures over 80 mm Hg. Decompression occurs rapidly, by venting a large valve to the atmosphere. During the resulting low pressure phase, there is a marked increase in arterial blood flow.

U.S. Pat. No. 4,624,244 and U.S. Pat. No. 4,941,458 teach of a device—and corresponding method of use—for an ambulatory patient, wherein the device comprises a cuff for placement around the lower calf and foot of a person suffering from circulatory problems. In this device, air bladders are pulsated about the lower calf and soft tissue of the foot by means of a pump and pulse-inducing flow control means. The cuff does not provide a boot as such and various fasteners are secured so that the cuffs fit snugly, but not so tight as to impair circulation of a foot. When the bladders are inflated, they will bulge inwardly toward the adjacent soft tissue to provide good pressure against the deep veins. US2003/0013997 provides a venous pump to promote circulation; a bladder placed under the sole of a wearer of such a boot inflates a cuff placed around a calf of the wearer of the boot whereby walking provides cyclical compression of the bladder, which in turn inflates the cuff. U.S. Pat. No. 6,589,194 teaches of a self-powered inflatable compression device for use in promoting circulation. However, this device—which comprises sequentially filled pressure sleeves situated about a leg is wrapped in bandage; it provides no support for ulcerated feet and provides a device that is suitable for indoor use.

Despite the known advantages of compressive forces applied to the legs and feet, there remains a need for simple, truly mobile device without the need for further boot arrangements, which enable ambulatory movement and conveniently do not depend on electrical power being available, either from batteries or mains supply. Additionally there is no system available operable to provide a boot or other form of footwear which enables the user to be supported whereby compressive forces encountered in walking do not compromise healing of an ulcerated wound or similar lesion.

The present invention seeks to address some of the problems encountered by prior art limb compression devices and methods. In particular the present invention seeks to provide a boot which can stimulate blood flow. A further object to the invention is to provide a boot with a sole which is adaptable to conform with various shapes and conditions of human feet. The present invention seeks to provide a new type of footwear that has a therapeutic benefit for diabetic patients with circulatory problems in their foot and also enables the technique of "off loading" the foot to assist in the healing of any wounds present.

The present invention further seeks to provide a boot that can improve arterial blood flow in a leg in order to treat ischemic pain and ulceration, and obviate the need for amputation, thereby eliminating the risks of surgery.

SUMMARY OF THE INVENTION

In accordance with a first aspect of the invention, there is provided a boot for comprising an upper, a blood flow stimulating element, and a sole element;

wherein the upper is operable, when a person is utilising the boot, to engage with and fixedly retain a calf portion of the leg of the wearer, whereby to enable offloading of the foot and to allow the foot to remain stationary with respect to the calf;

wherein the blood flow stimulating element is placed such that, in use, it is opposite the plantar plexus region of a foot;

wherein the sole element comprises a first upper element and a second lower element; the respective first and second sole elements being movable one with respect to the other and are connected to the blood flow stimulating element such that, in use, the blood flow stimulating element is caused to move with respect to a foot retained therein whereby blood flow within the foot is encouraged by the stimulating element abutting the plantar plexus region. Such blood flow will arise despite a lack of relative movement of the foot with respect to the lower leg, which is necessary and inevitable in a foot which is in good health. The blood flow stimulating element, by abutting against the plantar plexus of a foot in a pulsating fashion assists in venous and arterial drainage of the foot. By the provision of off-loading attributes, in use, there will be no pressure and shear forces generated between parts of the foot and leg as ambulatory action takes place.

Accordingly the main advantages of the invention arise from lack of relative movement between leg and foot whereby to prevent damage/further damage by way of tearing of skin etc. and to induce venous drainage of the foot independent of movement between leg and foot.

In one embodiment, the upper and lower sole portions define a bladder therebetween, whereby, movement of the respective upper and lower sole portions causes fluid to flow to and from the moveable sole portions to the blood flow stimulating element, whereby to cause a bladder or piston associated with the blood flow stimulating element, which in turn causes the blood flow stimulating element to abut against the plantar plexus in a pulsating fashion.

In another embodiment, the boot has a sole comprises a two part structure having upper and lower sole portions, wherein the lower portion is hingedly connected with the upper sole portion, wherein the lower sole portion has a connecting rod operable to cause directly or indirectly movement of the blood flow stimulating element. The connecting rod can drive a fluid pump comprising a piston operating within a cylinder; the lower sole portion being resiliently biased with respect to the upper sole portion whereby to enable the sole to return to a rest position after compression of the piston within the cylinder. The pump can cause a reservoir to be pressurised in the case of a gaseous fluid; alternatively, the pump can cause a bladder to be repetitively filled and emptied of fluid.

In the event that the pump pressurises a pressure storage tank; the tank can provide fluid to a bladder or piston associated with stimulating means via a valve; the valve being controlled to provide a timed release of pressurised fluid.

The sole can comprise a bellows-like structure, operable to enable a pressurised fluid to cause bladder to be filled and emptied of fluid.

The blood flow stimulating means may comprise one or more separate units, which may be filled either sequentially or simultaneously. Further blood flow stimulation units such as inflatable cuffs may be arranged about the about the upper of the boot whereby to increase control of the blood flow.

The moveable portion can conveniently comprise a bladder which is periodically inflated and deflated whereby to urge the bladder against the under-sole of the wearer of the boot.

Any pump arrangement may be configured such that the pump may pressurise a pressure storage tank; the tank providing fluid to the bladder via a valve. The valve is conveniently controlled to provide a timed release of pressurised fluid. In one embodiment, the pressurised fluid may be released to one or more bladders, either sequentially or simultaneously.

The present invention thus addresses some of the problems encountered by prior art limb compression devices and methods. In particular the present invention seeks to provide a shoe or a boot which can stimulate blood flow, in ambulatory motion by a wearer of the boots whilst enabling the foot to remain in an offloaded state.

It will be appreciated that those who have an ulcer or similar lesion of their foot will not want to use their foot in a normal fashion, whereby to enable the wound to heal. That is to say not all parts of the sole may be able to take loads. Additionally, the present invention conveniently is equipped with a sole portion which can be shaped by scissors, knife or saw whereby to reduce contact of the sole with the boot for load purposes.

BRIEF DESCRIPTION OF THE DRAWINGS

For a better understanding of the present invention, reference will now be made, by way of example only, to the Figures as shown in the accompanying drawing sheets, wherein:—

DETAILED DESCRIPTION OF THE INVENTION

In order to provide a better understanding of the present invention an embodiment of the invention will now be described. It will be apparent, however, to one skilled in the art, that the present invention may be practised without these specific details. This should not be construed to limit the present invention, but should be viewed merely as an example of a specific way in which the invention can be implemented. Well known features have not been described in detail so as not to obscure the present invention.

Figure 1:
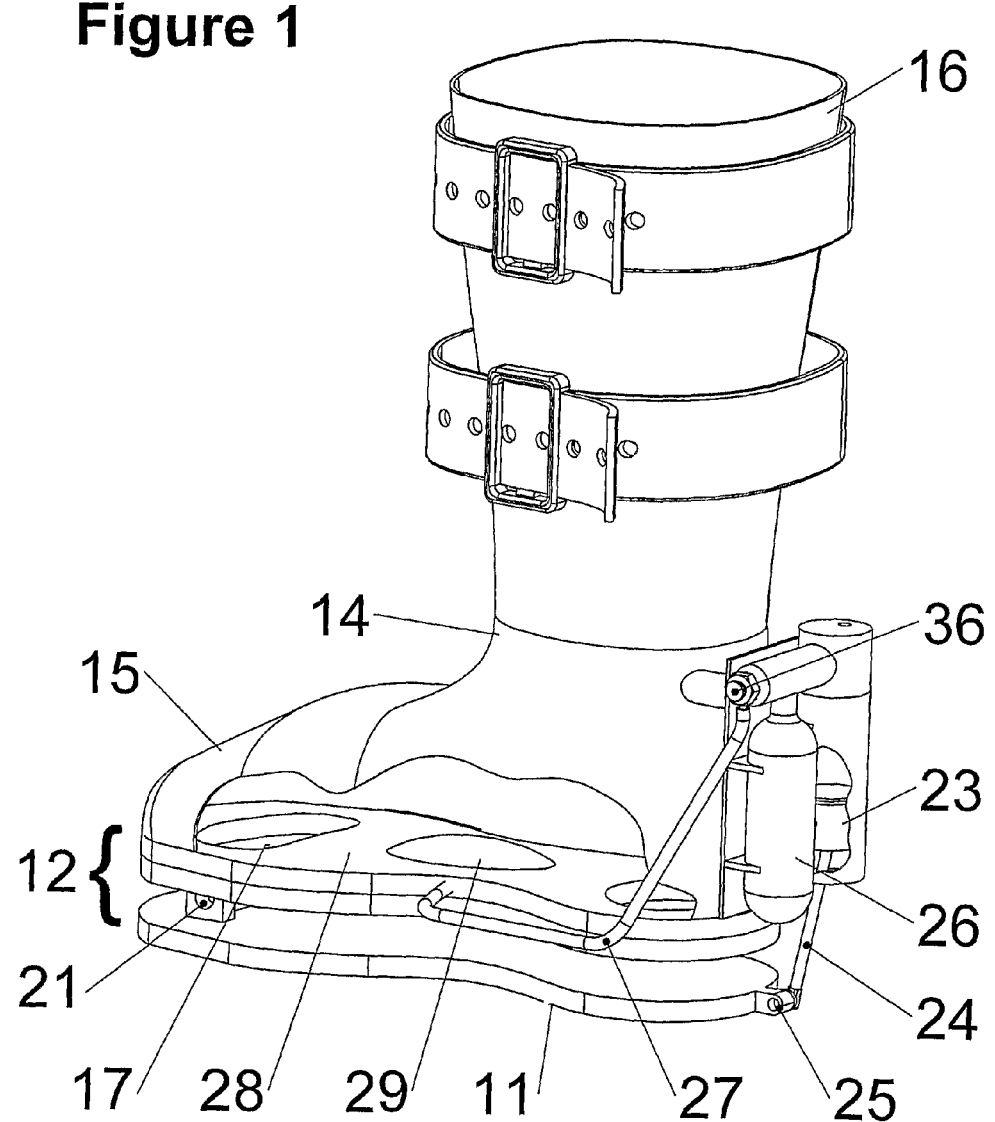
FIG. 1 is a perspective view, part cut-away, of a first embodiment of the present invention.

Referring now to FIG. 1, there is shown a first embodiment of the present invention, where there is shown a boot having a sole 12, upper 14 comprising a lower section 15 operable to cover the toes and metatarsals and an upper section 16 operable to encircle a lower leg portion (not shown) of the wearer of the boot. This particular embodiment is arranged for the support of a foot which is subject to an ulcer or similar lesion on the underside of the foot: the inner sole 28 of the boot is arranged to reduce load on the sole portion subject to ulcer or lesion. The areas of the foot most prone to the ulcers are the heel and main pad of the foot. Conveniently, this is enabled by shaping the inner sole, by means of a sharp knife or small saw, whereby to produce apertures 17 within the inner sole. Additionally, the uppermost portion of the upper provides support to the leg whereby to reduce loading upon the sole of the foot. Straps, not referenced, are fastened tightly about the calf, whereby to support the calf for effective off loading.

A bladder 29 arranged as a raised portion of the sole operates—when in use, with a foot placed inside—to abut, in a pulsing fashion, the plantar plexus, whereby to provide a rhythmic pressure to the plantar plexus of the foot, whereby to stimulate and encourage blood flow to and blood flow from the foot, in particular venous flow from the foot. The bladder is conveniently an air bladder: located under the plantar plexus, to pro-vide the necessary compression, for the pumping effect of the blood to occur. The bladder may comprise an integral part of the innersole. Other fluids can, of course be used, but this may provide complications; the compressibility of air or other types of gases is used to advantage in a preferred embodiment, but it is to be realised that various hydraulic arrangements can be realised, which may take other advantages of fluids into account whereby to provide a different pressure pulse, dependent upon the severity of the condition; a rapidly deployed pulse is known to be particularly effective for those suffering from deep vein thrombosis.

The first embodiment is shown with an under-sole element 11 which is hinged in a biased state by hinge or pivot means 21 in co-operation with a resilient element not shown: in use, repeated steps causes piston 23 attached by a connecting rod 24 to pivot 25 of the under-sole element 11 to feed pressurised air into a pressure storage unit 26 such that it becomes pressurised. Valve means indicated by reference numeral 36 operate such that a burst of pressurised air is directed via tube 27 to the bladder, whereby a brief pressure burst is realised whereby the bladder presses against the plantar plexus, whereby to cause arterial/venous stimulation.

Figure 1A:
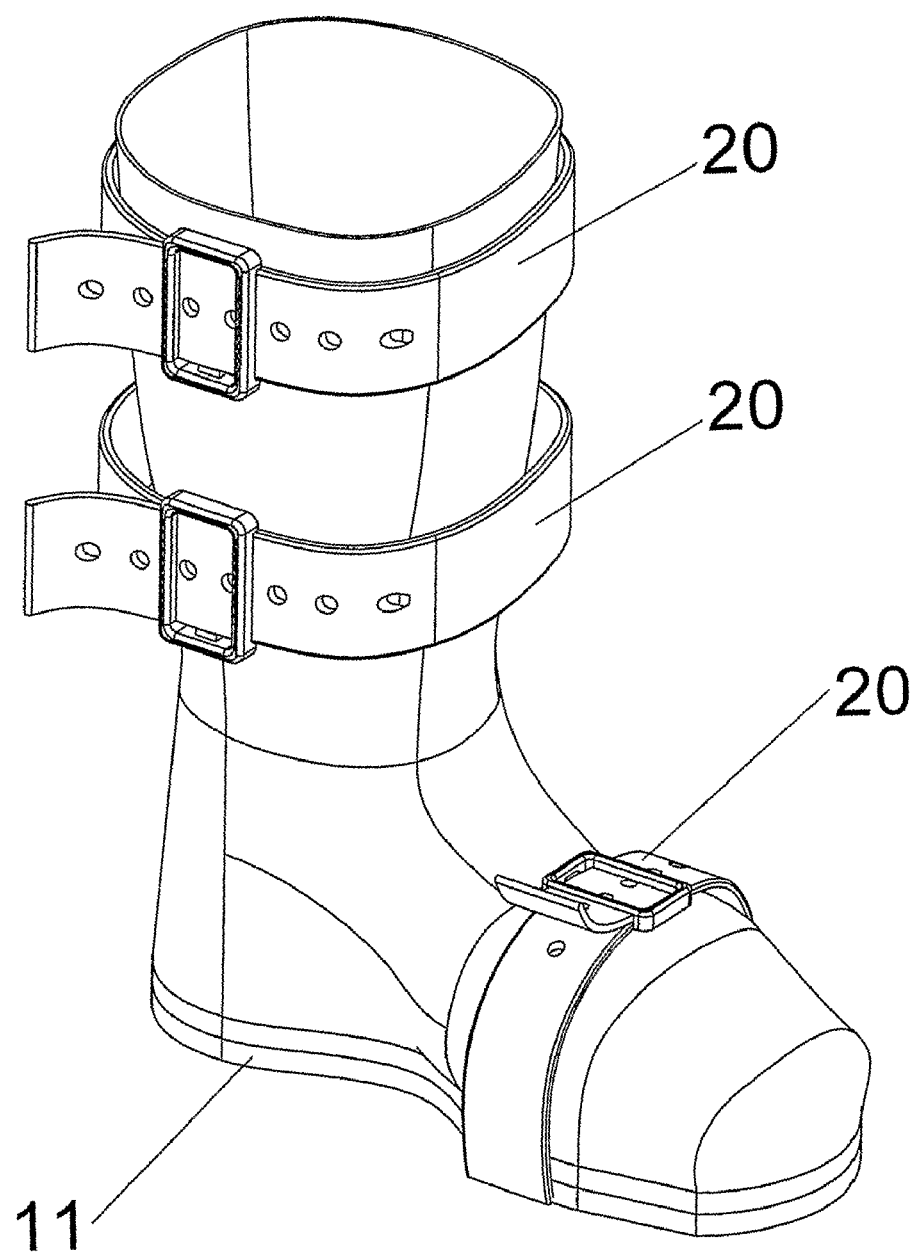
FIG. 1a shows the boot of FIG. 1 from another side.

FIG. 1a shows a perspective view of the boot shown in FIG. 1 from the opposite side. It can be clearly seen that the boot comprise a two part upper construction with a forward element 28 which extends from the front tip of the sole, across the upper part of the foot and extends upwardly whilst enveloping the sides, at least in part, whereby the rear upper extends from the sides and rear of the sole towards the rear and sides of the upper part of the boot upper. Straps 20 serve to enclose the respective upper parts together, whereby to engage the lower leg such that off-loading of the foot is ensured, whereby the chances of abrasion, tearing or otherwise of the foot against the sole of the foot is diminished or reduced altogether.

Figure 2:
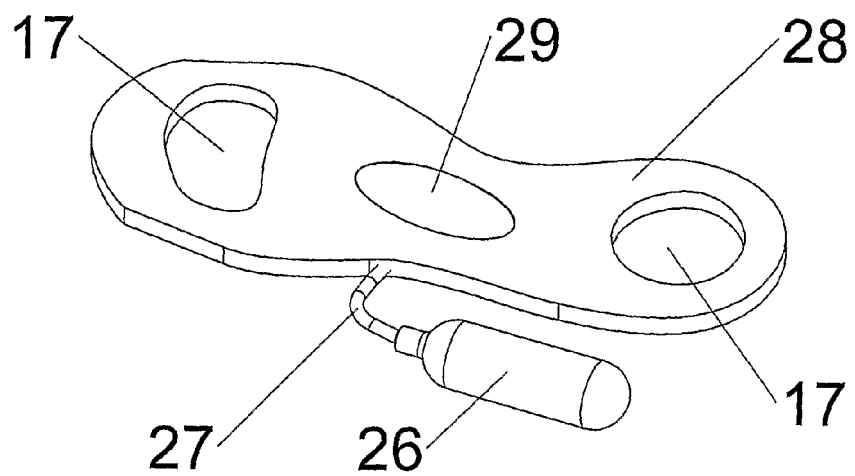
FIG. 2 is a perspective view of a sole in accordance with a second embodiment

FIG. 2 shows a second embodiment wherein there is provided a bellows-type sole 28 operable to be compressed in use, whereby to urge air under pressure into pressure storage unit 26, whereby to provide a source of compressed air. It will be appreciated that as a sole unit, the exact placement of the bladder is not of particular concern, since that can be provided within or associated with an inner sole, not shown. Conveniently, the upper surface 29 of this bellows sole 28 is manufactured of a rigid plastics material and has a port with which an input tube of a bladder element can locate—possibly being of a similar nature to the material of an under-sole portion, with the bellows side elements being initially formed of a further, more resilient types of plastic material. Conveniently, the sole portion 28 is manufactured in a two stage plastics manufacturing process, whereby to enable the upper, lower and bellows elements of the sole 27 to be simply and reliably manufactured. Indeed, the upper sole portion may be reinforced with a metallic, element, carbon fibre element or other form of reinforcement, as is known to those skilled in the art. Apertures 17 are shown as being defined in the sole, to reduce loading on the corresponding areas of the sole of the wearer of the boot.

Figure 3:
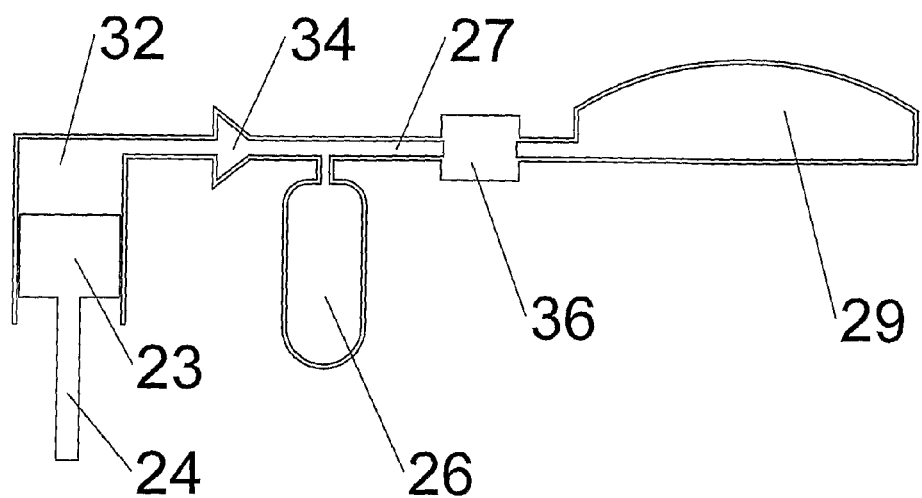
FIG. 3 is a schematic view of a pump arrangement in accordance with one aspect of the invention.

FIG. 3 shows a schematic diagram for the elements of a bladder system; a rod 24 connected at a first end to a lower sole element (not shown) and to a piston 23 at a second end receives an upwardly directed force. In use, upon contact of the sole with a ground or floor surface (not shown), the connecting rod urges piston 23 within cylinder 32; at the end of the stroke pressurised air is urged into the pressure storage unit 26. A one way valve 34 ensures that pressure is maintained within the pressure storage unit. Control means 36 enable the bladder 29 to be filled according to a variable or pre-defined duty cycle.

Conveniently, the bladder may be compartmentalised, whereby to provide a directional pulse in use of the bladder. The bladder situated under the plantar plexus may be linked to further bladders, arranged about the ankle or calf of the boot. Upper air bags to allow the boot to be more conformal to each user, and provide more effective off loading of the sole of the foot, by taking the weight of the body and transferring it directly to the sole of the boot. These could also be pulsed if clinical benefit is determined for a particular patient.

FIG. 4 shows a cross section through a simplified structure; boot 40 comprises a sole 12, upper 14 comprising a lower section 15 operable to cover the toes and metatarsals and an upper section 16 operable to encircle a lower leg portion (not shown) of the wearer of the boot. Sole 42 is connected via pivot 41 and is provided with a resilient spring element which transfers damped energy to a movable sole portion 44 which acts against the plantar plexus of a wearer of the boot.

By employing a resilient member, such as a coil spring, the forces arsing from the wearer are damped or reduced whereby the impact forces experienced by the sole are not transferred directly to the sole of the foot of the wearer of the boot. Other resilient members could be utilised such as leaf springs, gaseous balloons etc., whereby the plantar plexus can be stimulated in a more controlled fashion; the stimulation pulse may need to be instantaneous (especially for those with DIM or delivered over a pre-defined period. Indeed, other forms of devices operable to convert movement arising from ambulatory motion into stored energy can be employed; for example linear motion could be transferred to rotational motion, using a ratchet spring or other form of device to store the energy, conveniently using simple pressure cells and devices or dynamos could be employed; mechanical electricity generation devices could be employed.

Figure 4A:
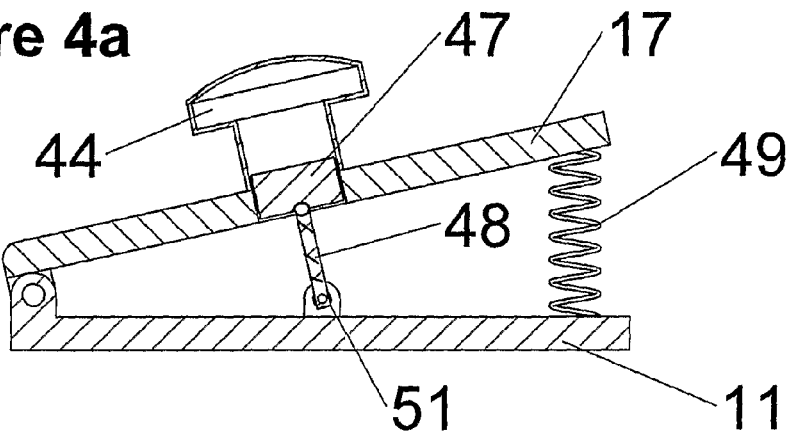
FIGS. 4a & b show two different types of driving the blood stimulating portion; and, FIG. 5 show the prevalence of ulcers upon a foot.
Figure 4B:
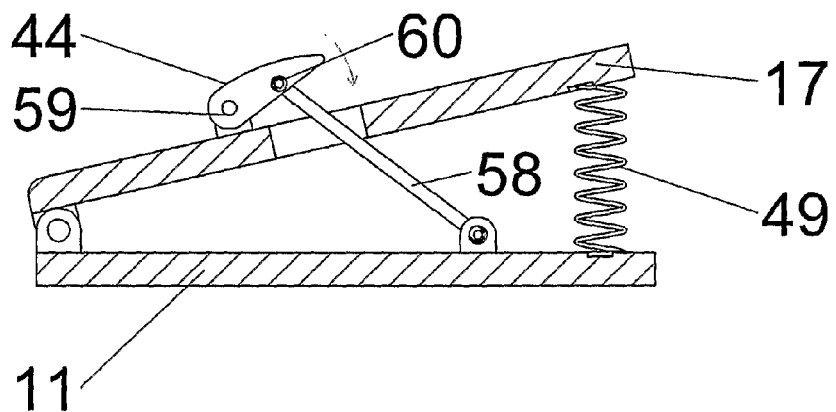
FIG. 4 shows a simplified example of a boot made in accordance with the invention.

FIGS. 4a and 4b show two alternate types of construction for the stimulating element which presses against the plantar plexus. In FIG. 4a, the stimulating element 44 comprises an air bladder: to cause the top section to move by approximately half a centimetre over an area of about 2 square centimetres, requires movement of 1 cc of fluid from the cylinder and piston assembly 46 and 47 to be extended fully; equivalent to a movement of 1 cm if the piston is 1 square centimetre in area. Piston 47 is connected via a connecting rod 48 and is operable to pass fluid to the bladder upon compression and to receive fluid upon relaxation—assisted by a return spring schematically indicated at 49. The distal end of the piston is connected to the sole 11 via hinge element 51. Conveniently, both expanding element 44 and the hinge element 51 can be securely fastened in one of a number of positions with respect to the upper sole element and lower sole element, respectively. With respect to FIG. 4b, the stimulating element 44 comprises an arcuate yet cushioned element which is fixed at one point 59 and a connecting rod 58, attached to the sole at hinge element 51 in much the same way as that described with reference to FIG. 4a is attached to a lower point of the arcuate member at a pivot point 60 and is so fastened whereby, applying principles of levers and an offset axis of rotation of the pivot point 60 to the pivot axis 59 of the arcuate member enables the arcuate member to pivot in a limited fashion, whereby to enable the stimulating element 44 to abut the plantar plexus of a person wearing the boot, whereby, in use, to encourage blood flow in the extremities of the foot. It will be appreciated, that the amount of movement of the arcuate element can be readily adjusted using different lengths of offset of one pivot axis with respect to the connecting rod connection point. Equally, the stimulating element 44 and the hinge element 51 can be securely fastened in one of a number of positions with respect to the upper sole element and lower sole element, respectively. Whilst the connecting rods are shown as being of single construction, there may be an instance where they are manufactured in a two part form with a damping mechanism therebetween, whereby sudden shocks are absorbed.

Figure 5:
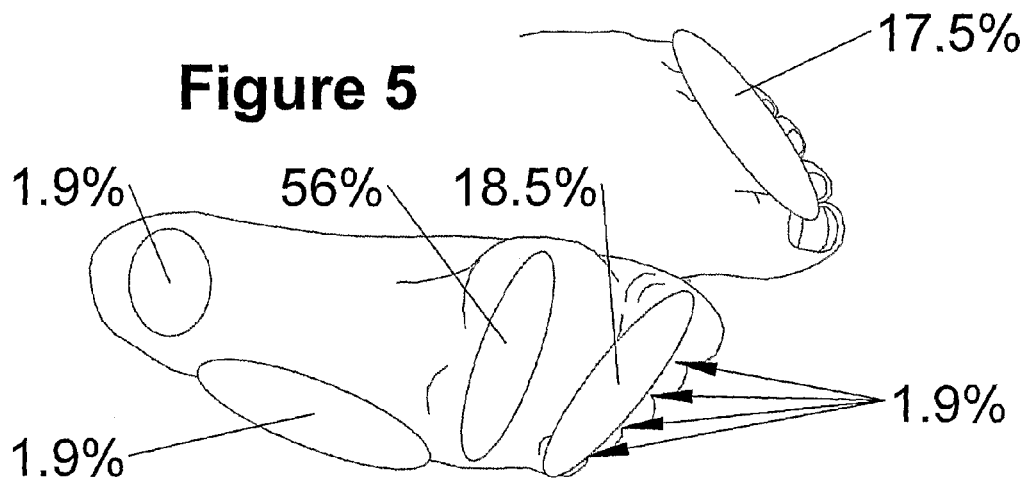

With reference to FIG. 5, there is shown, in outline, views of the foot from above and from below, with a percentage of prevalence of ulcers that were present in a sample of patients having foot ulcers conducted by Layery et al (2208). Further studies in this area are known from Dr. David G. Armstrong, Dept. Orthopaedics at the University of Texas Health Science Center, see for example, Improvement in healing with aggressive oedema reduction after debridement of foot infection in persons with diabetes, Archives of Surgery, December 2000 Vol 135, p 1405. Ulcers can also arise in the interdigital areas, as indicated in the lower right portion of the Figure. In the case of those suffering from oedema, it may be necessary to provide the boot with a two (or more) part construction; a sole portion is detachable form the upper; whereby placement of the boot can be enabled, without severe discomfort, by the placement of the upper around the foot and calf prior to connection with the sole. Simple quick release connectors can be used for this purpose; where calf or leg bladders are employed, fluid-tight connections means must be used in the event that the calf and sole are completely separable.

It should also be mentioned that the construction of the boot should be such that the foot can perspire; with poor circulation feet will not perspire normally; it has been found that additional vents are beneficial to remove moisture, generally. It will also be appreciated that an additional forced air supply form the pressurising device (either directly of indirectly will assist; an overly moist skin will break down quicker than normal dry skin, which will be an important factor with those who are susceptible to ulcers.

The invention claimed is:

1. A boot for receiving a foot of a user comprising
an upper, a blood flow stimulating element, and a sole element;
wherein the upper, when the boot is in use, engages with and fixedly retains a calf portion of a leg of the user to offload weight of the user from the foot;
wherein the blood flow stimulating element is, in use, opposite a plantar plexus region of the foot; and
wherein the sole element comprises a first upper element and a second lower element; the respective first upper and second lower sole elements being movable with respect to each other and being operably connected to the blood flow stimulating element wherein, in ambulatory use, relative movement of the first upper and the second lower sole elements causes movement of the blood flow stimulating element to move with respect to the foot, with blood flow within the foot being encouraged by the stimulating element abutting the plantar plexus region; the stimulating element comprising part of an innersole of the boot, the innersole having an aperture to enable the stimulating element to be defined therethrough.

2. A boot according to claim 1 wherein the blood flow stimulating element comprises a bladder between the upper and lower sole portions, with movement of the respective upper and lower sole portions causing fluid to flow to and from the bladder which is thereby periodically deflated and inflated to urge the stimulating element against the plantar plexus region of the foot of the wearer of the boot.

3. A boot according to claim 1 wherein the second lower element is hingedly connected with the first upper element, wherein the second lower element has a connecting rod operable to cause, directly or indirectly, the blood flow stimulating element to move.

4. A boot according to claim 3 wherein the connecting rod drives a pump comprising a piston operating within a cylinder; the second lower element being resiliently biased with respect to the first upper element to enable the sole to return to a rest position after compression of the piston within the cylinder, with the pump providing pressurized fluid to cause bladder to be filled and emptied of fluid.

5. A boot according to claim 4 wherein the pump pressurizes a pressure storage tank, with the tank providing the fluid to the bladder via a valve.

6. A boot according to claim 2 wherein the sole comprises a bellows-like structure, operable to pressurize fluid to cause bladder to be filled and emptied of fluid.

7. A boot according to claim 6 wherein the sole comprises a pressure storage tank, with the tank providing fluid to the bladder via a valve.

8. A boot according to claim 4, wherein the valve is controlled to provide a timed release of pressurized fluid.

9. A boot according to claim 1, further comprising a separate inner sole that comprises a material that provides for apertures to be defined therethrough to thereby enable cutouts to be defined therein that reduce contact of selected areas of the sole with the sole elements.

10. A method for using a boot to assist in ambulatory venous drainage, the boot comprising an upper, a blood flow stimulating element, and a sole element; wherein the upper, when the boot is in use, engages with and fixedly retains a calf portion of the leg of the user to offload weight of the user from the foot; wherein the blood flow stimulating element comprises part of an innersole of the boot, the innersole having an aperture to enable the stimulating element to be defined therethrough and is, in use, opposite a plantar plexus region of the foot; and wherein the sole element comprises a first upper element and a second lower element; the respective first upper and second lower sole elements being movable with respect to each other and being operably connected to the blood flow stimulating element;

the method, in ambulatory use, comprising the step of alternating depression of the upper element upon the lower sole element thereby to induce movement of the blood flow stimulating element abutting the plantar plexus region, thereby to encourage blood flow within the foot.

* * * * *